United States Patent
Shanbaky

(10) Patent No.: US 7,980,745 B2
(45) Date of Patent: Jul. 19, 2011

(54) BROAD SPECTRUM FIBER OPTIC BASE LASER ILLUMINATION

(76) Inventor: Ramsey Shanbaky, San Francisco, CA (US)

( * ) Notice: Subject to any disclaimer, the term of this patent is extended or adjusted under 35 U.S.C. 154(b) by 453 days.

(21) Appl. No.: 12/215,910

(22) Filed: Jun. 30, 2008

(65) Prior Publication Data
US 2009/0054957 A1 Feb. 26, 2009

Related U.S. Application Data

(60) Provisional application No. 60/958,046, filed on Jul. 3, 2007.

(51) Int. Cl.
*G02B 6/00* (2006.01)
(52) U.S. Cl. .......... 362/581; 362/231; 362/84; 362/551; 362/582
(58) Field of Classification Search .................. 362/553, 362/551, 552, 555, 231, 572, 575, 577, 581, 362/582; 600/249, 10–12; 385/38, 901, 385/902
See application file for complete search history.

(56) References Cited

U.S. PATENT DOCUMENTS

| | | | |
|---|---|---|---|
| 4,917,448 A * | 4/1990 | Oppenheimer | 385/116 |
| 5,901,261 A * | 5/1999 | Wach | 385/38 |
| 5,968,039 A * | 10/1999 | Deutsch et al. | 606/17 |
| 6,015,403 A * | 1/2000 | Jones | 606/4 |
| 6,540,390 B2 * | 4/2003 | Toth et al. | 362/552 |
| 7,618,176 B2 * | 11/2009 | Ng | 362/558 |
| 7,672,713 B2 * | 3/2010 | Furnish | 600/476 |
| 7,758,224 B2 * | 7/2010 | Hama et al. | 362/555 |
| 2005/0143637 A1* | 6/2005 | Feldon et al. | 600/406 |
| 2008/0051632 A1* | 2/2008 | Ito et al. | 600/114 |

* cited by examiner

*Primary Examiner* — Ali Alavi
(74) *Attorney, Agent, or Firm* — G Kenneth Smith

(57) ABSTRACT

The present invention is an illumination device designed to provide efficient illumination in confined spaces and methods of using such a device. The devices of the present invention comprise a laser light source of a specifically selected wavelength or wavelengths, optical fiber(s) and one or more light converters to convert the input laser light to broad spectrum white light or a specific desired wavelength. The light converter may be integral/modular with the fiber optic assembly. The light converter may be constructed of phosphors, nanocrystals or other energy converters which are embedded within a transport material such as polymer or glass.

19 Claims, 4 Drawing Sheets

BROAD SPECTRUM FIBER OPTIC BASE LASER ILLUMINATION

This application claims benefit under 35 USC §119(e) of the U.S. Provisional patent Application Ser. No. 60/958,046 filed Jul. 3, 2007.

FIELD OF THE INVENTION

The present invention relates to the generation of broad spectrum light for illumination purposes more specifically for illumination for ophthalmology applications.

BACKGROUND OF THE INVENTION

The use of illumination sources is widespread. In the medical industry illumination uses range from large overhead light sources for the operating arena to small sources delivered endoscopically through fiber optic bundles. Bulb based light sources encounter difficulties when focused into small fiber bundle because this type of light source illuminates in all directions. Historically, complicated optical focusing schemes using mirrors, lenses or a series or lenses and mirrors have been utilized to focus omni-directional light sources into fiber bundles. These schemes for illumination are problematic in that these schemes are usually not very efficient and much of the light is lost as heat. In addition, fiber optic bundles which are utilized in these systems are not very durable and can be very difficult to assemble without breaking. Fiber bundles also present a size constraint as well.

With the advent of solid state light sources (e.g. light emitting diodes (LED), white LED) much development has taken place to convert the monochromatic light output of an LED into broad spectrum white light. These sources are very efficient and compact, but as with bulb based light sources, they are very difficult to efficiently focus into a small fiber optic. The size of the light source is therefore limited to the emitter size of a diode or a number of diodes stacked together.

The laser was invented nearly 50 years ago and in the intervening time many different wavelengths of highly directed and focused light have been generated. Furthermore, laser technology has become more cost effective with the production of laser diodes and solid state laser technology.

Light sources have been used for many years during ophthalmic procedures. Particularly in vitreo-retinal surgery stand alone light sources attached to needles have been used to locate the anatomy of interest and to illuminate the general area of interest during a procedure. Current light sources often employ a light bulb powered by an electrical power supply. These light bulbs can be xenon, halogen or metal halide bulbs. There are many limitations of the currently marketed light sources such as the fact that the light emitting from the bulb spreads out in all directions making it difficult to focus the light into small fiber optics for insertion into the eye. Corrections for this problem often entail surrounding the bulb by a parabolic mirror and attempting to focus the light into a high numerical aperture fiber bundle. Unfortunately, the size of the light emitted from the bulb limits the amount of light to be focused into the smaller fiber bundle. The coupling between the light source and the fiber is generally very inefficient and results in light being converted into heat on the fiber connector. Another limiting factor in this design is the output of the light from the fiber. The numerical aperture (NA) of the fiber limits the output of the light to a cone corresponding to the fiber NA. Thus, a physician using this type of device would only be able to see the area illuminated by the NA of the fiber and nothing wider. Bulb based sources also emit light from the ultraviolet (UV) to the infrared (IR). Much of the light is harmful and wasted because they are invisible to the eye. Light sources that emit at these wavelengths require filtering to protect the eye from these harmful wavelengths.

Bulb based light sources and fiber bundles also have reliability limitations. The light bulbs burn out after a few hundred hours or less. In addition, fiber bundles are very brittle. If the fiber bundles break the total light output is significantly reduced. Additionally, the design is limited by the size of the fiber bundle such that if the fiber bundle is made smaller the total amount of light emitting from it decreases.

US Patent Application No. 2008/0051632 describes an illumination device comprising a laser light source with a fluorescent substance for illumination and visualization for endoscopic examination.

U.S. Pat. No. 5,651,783 describes a fiber optic integrated phacoemulsification system which incorporates fiber optic bundles that transmit visible light to enhance visualization by intraocular illumination.

U.S. Pat. No. 6,015,403 describes a probe for ophthalmic surgery utilizing a laser light source or an illumination source and an optical fiber for transmitting light from the light source to the eye to be treated.

There is a need for the efficient delivery of broad spectrum light for illumination in small compact confined spaces, like those required for ophthalmic surgery. The present invention provides solutions to many of the problems that exist in the currently marketed illumination devices. The illumination devices of the present invention are laser based so focusing the beam into a single small fiber can be more easily accomplished. Coupling efficiencies of 96% or greater can be achieved, which limits the problem of excess heating at the coupler. The use of lasers as a light source also greatly increases the electrical efficiency because all of the light is used for the output and little or no energy is wasted. Single fibers may be coated and structurally supported so mechanically the fibers are much stronger than fiber bundles that can be very brittle. Laser lifetimes are generally around 10,000 hours rather than the few hundred hours of life for a bulb based system. The laser light used in the present invention is safer to the eye than UV wavelengths. The white light spectrum is controlled by one or more light conversion medium so no filtering may be required. Inherently there are less harmful wavelengths emitted to the treatment area. Finally, because the light source effectively is at the output of the device, the light output can be controlled to be as wide as possible providing the largest possible field of view for the physician.

SUMMARY OF THE INVENTION

The present invention solves the problem of compact efficient light sources that can be used in small spaces. The devices of the present invention comprise a laser light source of a specifically selected wavelength or wavelengths, optical fiber(s) and one or more light converters to convert the input laser light to broad spectrum white light or a specific desired wavelength. The light converter may be integral/modular with the fiber optic assembly. The light converter may be constructed of phosphors, nanocrystals or other energy converters which are embedded within a transport material such as polymer or glass.

By varying the size of the light converter and the concentration of conversion materials the output stream and brightness can be controlled. By varying the relative positions of the system components, conversion efficiency can be controlled. The design of the optic fiber assembly and light converter can be adapted to facilitate use in various applications such as endoscopy, laproscopy and minimally invasive medical procedures.

FIGURES

DETAILED DESCRIPTION OF THE INVENTION

Figure 1:
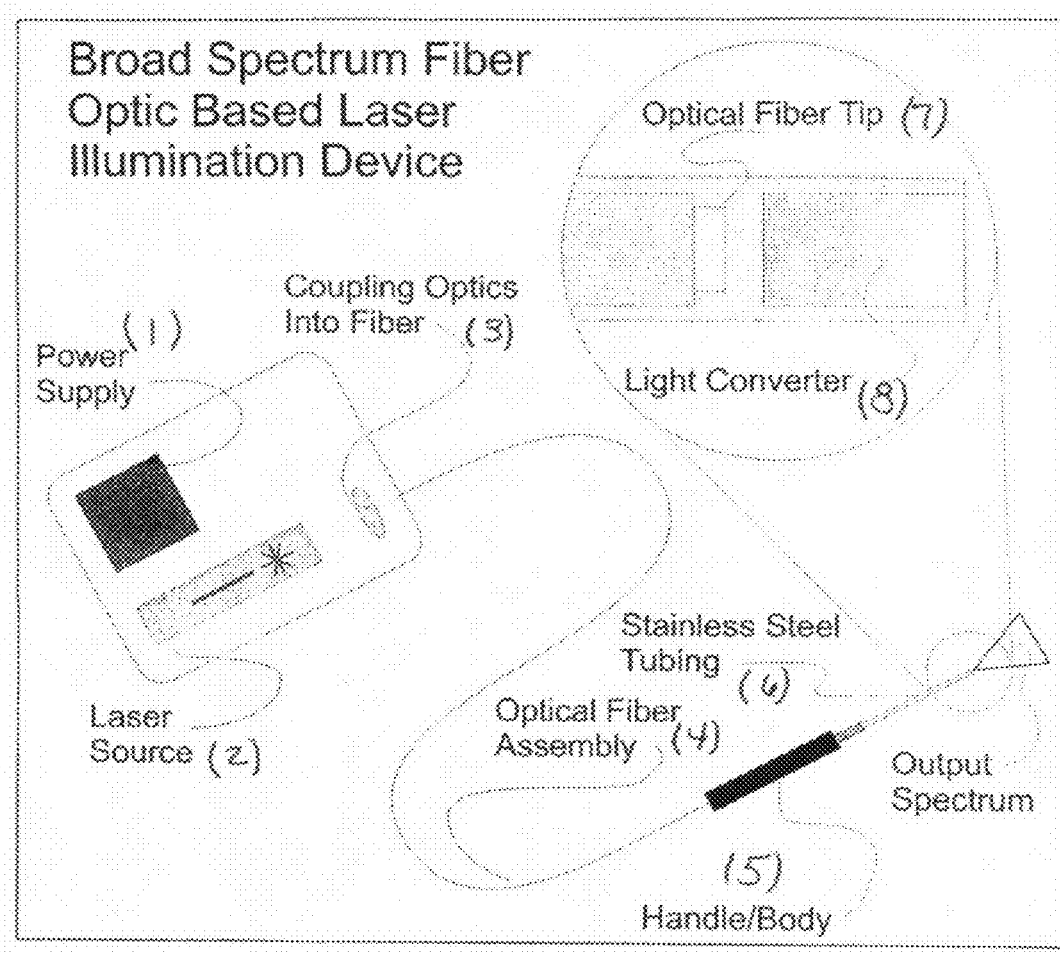
FIG. 1 is a schematic diagram of a preferred embodiment of the illumination device of the present invention.

The devices and methods of the present invention permit efficient delivery of broad spectrum light for illumination in small compact confined spaces. While the illumination devices of the present invention have broad applicability to a variety of medical or dental application the illumination devices of the present invention have particular applicability in the field of ophthalmology. The devices of the present invention comprise laser light source(s), optical fiber(s) and light converter(s). The light converter will convert the input laser light to broad spectrum white light or to specific desired wavelength depending on use. The general assembly of the components is as follows. First the laser which is connected to a power supply is aimed through some focusing or fiber coupling optics into the fiber optic. At the tip of the fiber optic, there is a polymer and light conversion medium mixture that will convert the laser light into broadband white light.

In the illumination devices of the present invention the laser includes many variations of laser light. The lasers that can be utilized in the illumination devices of the present invention include but are not limited to fiber lasers, frequency doubled fiber lasers, diode lasers, frequency doubled diode lasers or combinations thereof. In a preferred embodiment the laser is a diode pumped solid state laser. This variety of laser is cost effective and an efficient and reliable laser light source. In ophthalmologic applications this laser comprises a Neodymium YAG laser that emits at 946 nm and it frequency doubled to 473 nm. In order for the light conversion medium to produce white light, laser light with a wavelength shorter than the white light produced by the conversion medium is required. Thus in the preferred embodiment the laser light source can emit any wavelength from the ultraviolet spectrum through about 488 nm. As the wavelength increases above 488 nm the white light produced by the conversion medium will be less efficient and appear bluish-green in color. For ophthalmologic uses lasers with wavelengths between 473 and 488 are desired because they have a low value on the photoaphaic curve (low phototoxicity for the eye). These sources are easily manufactured and have available wavelengths with sufficient power output. Up to 1 watt of optical power is commercially available in 473 nm. In a preferred embodiment of the illumination devices for ophthalmologic uses the wavelength of 473 nm was selected because it is the most eye safe wavelength that will still efficiently excite the conversion medium. Other blue lasers can generate brighter white light 450 nm thru 460 nm are desirable wavelengths. Four (4) watt commercially available 457 nm lasers can increase light output significantly. Lower wavelengths like 405 nm are used in LED technology to generate white light, but are not as safe for ophthalmologic uses.

FIG. 1 illustrates a preferred embodiment of the device of the present invention. In this embodiment the device comprises a power supply (1), laser light source (2), a coupling device (3) for directing the laser light into an optical fiber (4), a handle (5), a protective jacket (6), an optical fiber tip (7) and light converter (8).

Figure 2:
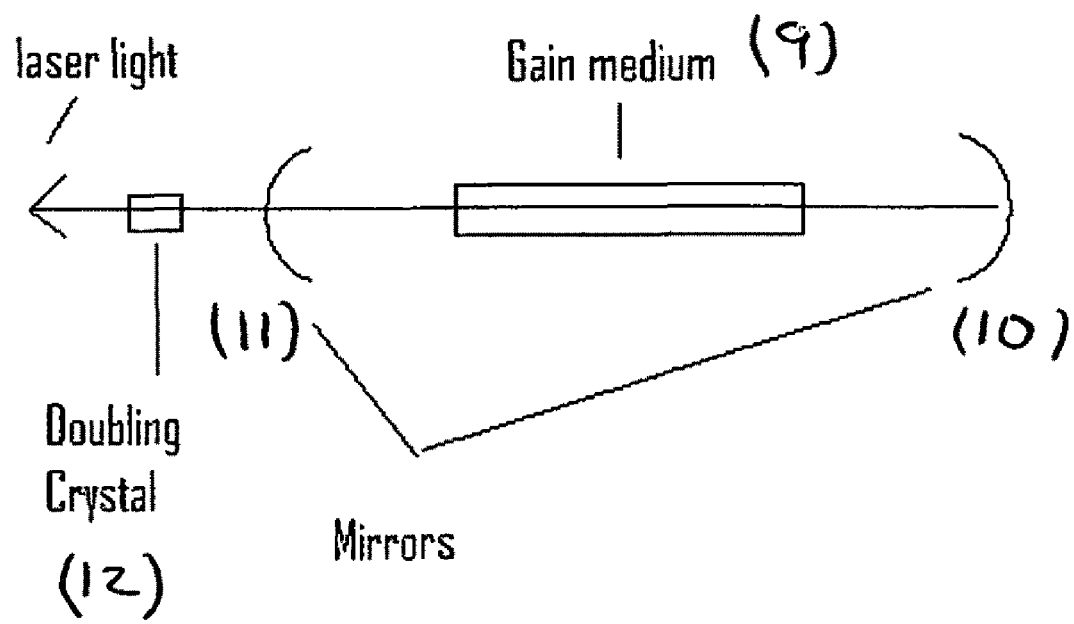
FIG. 2 is a schematic diagram of a preferred embodiment of the laser light source.

The laser may be assembled as a gain medium (9) that is placed between two mirrors (10, 11) to form a resonator as shown in FIG. 2. A frequency doubling crystal (12) may be placed either inside or outside of the resonator to provide the desired wavelength. A lamp, diode, laser or some other light source (pump source (13)) is used to illuminate the gain medium which then emits the laser light.

In preferred embodiments of the present invention the laser light source is focused into a fiber optic. One or more fiber optics can be used. The diameter of the core fiber may be about 50 um and larger, preferably in a ranger of about 50 um to about 1000 um, more preferably between about 100 um and about 300 um. The brightness of the light output is dependent on the core size of the fiber used and the output power of the laser. Brightness is a function of power and area of light output. The brightness will increase if a smaller fiber is used. Brightness and total light output are different though. If the size of the fiber is increased and the total area of phosphors used is higher than it will appear brighter to the eye as there is a larger area that is illuminated. If a smaller fiber is used the light output from the phosphors appear more like a point source with light emanating in all directions from a small point. When a larger fiber is used the light coming out of the phosphors appears more like cylindrical source. It still has the same total lumens of light coming out, but because a larger area is exposed it appears brighter.

Brightness is a non-quantitative explanation of light intensity. Quantitative light intensity measurements are called irradiance, which is total power of light per unit area; illuminance which is total luminous flux per unit area and lumenous flux which is the measure of total luminous power output corrected for the sensitivity of the human eye. Illuminance and lumenous flux use a weighted function of human eye sensitivity per wavelength to calculate the perceived brightness to the human eye. Irradiance is total optical power per unit area regardless of wavelength. Luminous intensity is total lumens/steradian. Because lumenous flux measurements take into account eye sensitivity to wavelength the total "brightness" of the laser source can be increased dramatically upon conversion to white light. Since illuminance is the total lumens per unit area, decreasing the total exposed area while keeping the total luminous flux constant will increase illuminance. Thus increasing the area of light converters exposed to laser light will increase the total luminous flux.

In one embodiment of the present invention about 70 mW of 473 laser light can achieve about 2000 foot candles of light output, which is approximately 28 lumens of total light output. The current light probes can produce about 4-15 lumens of light at the tip. On the higher end this is higher than commercially available products. Embodiments of the present invention have a peak efficiency number of about 400 lumens per 1 Watt of laser optical power. Utilizing appropriate cooling mechanisms the illumination devices of the present invention can achieve 400 lumens with a commercially available 473 nm laser or as much as 1600 lumens with commercially available 457 nm lasers. Multiplexing these systems into single fibers can achieve even higher light outputs. Appropriate cooling would be desirable in these schemes to keep efficiency numbers high. In embodiments of the illumination devices of the present invention a 1 Watt 473 nm laser can produce 400 lumens of light output in a 23 ga needle in 350 um diameter cross-sectional area.

In the illumination devices of the present invention it is desirable to have the optical fiber(s) housed in a protective jacket. Preferred protective jackets include needles whose size depends upon the particular application of the illumination device. Heavier gauge needles are more robust but bigger which may be a hindrance to their use in confined spaces. In ophthalmologic applications a range of needle sizes may be use. The only limitation on the protective jacket is the size of the fiber inside. The limitation in the fiber size is dictated by the ability to focus the laser into a small spot. With a very low M^2 laser it can be focused into a single mode fiber The lower range of the fiber outer diameter is about 100 um. Therefore, a protective jacket such as a needle may be as small as 34 gauge. With lasers of higher M^2 larger core fibers can be used to get better coupling efficiency In a preferred embodiment the illumination device for opthamologic use provides a 23 gauge needle for housing the fiber optic. This size needle provides rigidity while being safe in that it is not too large to cause excess trauma. In a preferred embodiment a 200 um core fiber with a total outer diameter of 240 um may be selected as the fiber to fit into a 23 gauge needle. With the proper focusing scheme any size fiber and jacketing could be used. Optionally the protective jacketing may be covered with various coatings that could provide among other benefits, added reflectivity, strength or flexibility as the particular application dictates. A hollow waveguide such as a capillary tube made of silica or polymers whose inner diameter is coated with a highly reflective material may be used to house the light conversion medium and fiber instead of a needle. This configuration may provide better forward transmission of converted light. A glass capillary may be used to house the mixture of light conversion medium and the fiber optic. The glass capillary could be used as a coated medium to filter out various undesirable wavelengths of light.

Flares, angles, tapers and other geometry can be made to affect the shape and direction of the light output to optimize efficiency and space utilization. A flare at the tip will block light that is going backwards and reflect it forward approximately at the angle of the flare. This can be used to control the width of the output cone of light. An angle cut at the tip will reflect the light to one side of the tip. This could be useful to direct light to the inner diameter of a tube or tube-like geometry. A taper will condense the light into a smaller output spot. This may be used to concentrate light into a smaller area. A lensed output could collect, concentrate or expand the output light from the phosphors. Many different types of lenses could be used to utilize these effects. A convex spherical lens, ball lens or gradient index lens would help collect the light or focus it. A concave spherical lens would widen the light output. Small elliptical mirrors at the tip can help control the light output as well.

Because the phosphors do not convert 100% efficiently some of the light energy will be converted into heat. If the laser power is high enough heat can be detrimental to the conversion process which will render the effect of the phosphors null. To combat this effect a heat sink can be used around the phosphors to pull excess heat away and allow the phosphors to work efficiently. This heat sink could be any material with a high thermal transfer coefficient. Examples of heat sinks that may be used in the devices of the present invention include but are not limited to metals, such as, copper, aluminum or silver, or ceramics like aluminum oxide or synthetic diamond. A fan or a thermoelectric cooler could also be used if the application permits. For certain medical applications the use of the device may be in an aqueous environment which will cool the tip slightly.

Figure 3:
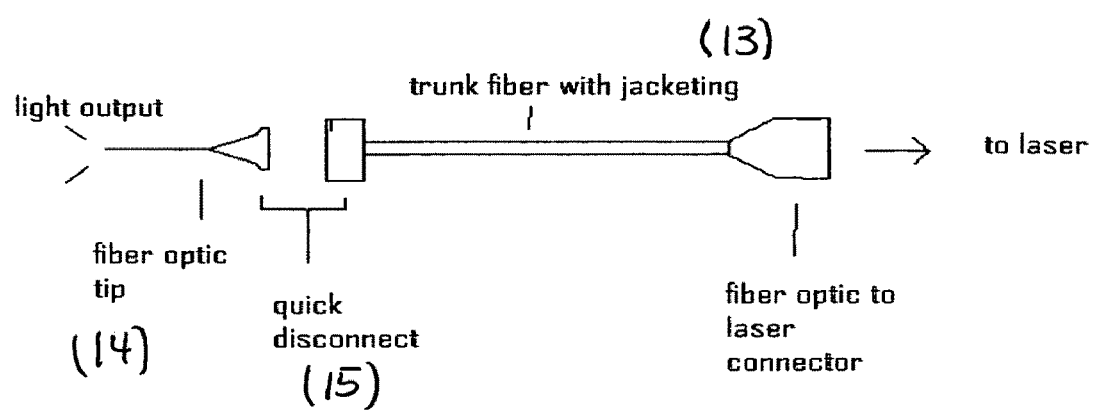
FIG. 3 is a schematic diagram of a preferred embodiment of the illumination device with a protective jacket and a removable fiber optic tip.

The fiber optic portion of the device may be arranged in a variety of ways. In addition to the protective jacketing, the illumination devices of the present invention may include among other options, connectors and disposable tips. One embodiment of the present invention utilizes a trunk optical fiber (13) that connects the laser to a fiber optic tip/light conversion medium combination (14) as shown in FIG. 3. This configuration of the illumination device includes a quick connect device (15) which permits removal and replacement of the fiber optic tip. The longer and more expensive trunk fiber can be re-used while the fiber optic tip can be disposed and replaced by another tip, thus allowing simple and quick changes and modifications to the output light from the fiber optic tip. The light could easily be manipulated to be focused, scattered, red-shifted, blue-shifted, angled output, attenuated, collimated, bent, reflected or any other modification. This allows the physician the ability to quickly change his light source to cater to his needs during a procedure. This quick disconnect mechanism may include lenses to refocus the light into the fiber upon connection. Spherical, gradient index or ball lenses may be used. In medical applications, the quick disconnect mechanism may also include a sheathed area to make sure the sterile operating field is maintained.

Light conversion media are those materials when the appropriate laser light impinges thereupon the media's spectra are broadened to the desired output spectrum The light conversion media used in the present invention include but are not limited to crystals, quantum dots, phosphors or any combination thereof. The light conversion material may be placed anywhere in the path of the laser light as long as the desired conversion from laser light to light of a different wavelength or wavelengths (such as white light) is achieved. In a preferred embodiment of the present invention the light conversion medium may be located at the fiber optic tip. The light conversion medium may be phosphors that are in powder form encapsulated in a polymer. This configuration optimizes the amount of light illuminating the treatment site. By manipulating the shape, location and concentration of the light conversion medium different effects can be achieved. By manipulating the shape, location and concentration of the light conversion medium different effects can be achieved. Furthermore, the light conversion medium can be mixed with various polymers and cured or molded into various shapes. Exemplary polymers include, but are not limited to silicone, epoxy, superglue or other liquids that can be mixed with light conversion solids to form solid compositions with the light conversion medium entrained. The mixture of phosphors and silicone or epoxy can be molded or shaped to achieve similar effects as above. By shaping the mixture into a semi sphere or spherical lens light can be focused or collected. By changing the concentration of phosphors in the mixture the light color can be changed. With a lower concentration of phosphors more blue light will leak out giving the light a bluish hue. If the concentration of the phosphors is increased the light output will have a more yellowish hue. For medical uses the light conversion material mixture is preferably biocompatible. Preferred phosphors are non-lead based Eu-doped silicates, which have no cytotoxicity effect when encapsulated. Other light conversion materials that are lead based may be used for non-medical applications of the illumination devices of the present invention.

In the case of ophthalmology, wide angle bright light is desired to have the largest field of view. Output angles can be anywhere from 0 degrees or collimated light to 360 degree light output. Currently marketed devices for ophthalmologic application have a maximum light output angle of 0.66 numerical aperture (NA) or about 40 degrees half angle, because they are limited by the intrinsic light output cone angle of the fiber optic. The half angle is the angle of light output from the optical axis of the device. The devices of the present invention are not limited in the ranges of angles that can be produced. The device of the present invention may elicit light at angles that exceed 0.66 NA or greater than about 40 half angle. The device of the present invention may have light output angles of about 80 degrees to about 360 degrees full angle. The device of the present invention may have light output angles of about 150 degrees to about 360 degrees full angle. The device of the present invention may have light output angles of about 250 degrees to about 360 degrees full angle. Putting the light source on the tip of the fiber optic obviates any limitation to the angle of light coming out of the illumination devices of the present invention.

By surrounding the light conversion medium by a reflective material or a needle with reflective material coated on the inside the light can be directed to the desired location. In this embodiment the light conversion material is surrounded by a glass capillary and a stainless steel needle for protection and easy insertion into the eye.

The illumination device of the present invention may optionally include additional components depending on the application and use of the device. For example, a base plate to which the laser and optics may be attached to insure correct alignment and to dampen vibration may be included in the illumination device. A cover which serves to protect the laser and provide aesthetics may also be included. In some embodiments of the illumination device of the present invention it may be desirable to utilize optical devices to couple the laser to the light carrying fiber. A spherical lens or combination of spherical lenses, aspheric lens or gradium lenses can be used to effectuate such coupling. Such coupling optics may be held in place by an optics holder which may also serve to align the coupling optics. A fiber connector may be used to align and hold fixed the fiber optic, while a fiber coupler may be utilized to align and hold the fiber connector.

Figure 4:
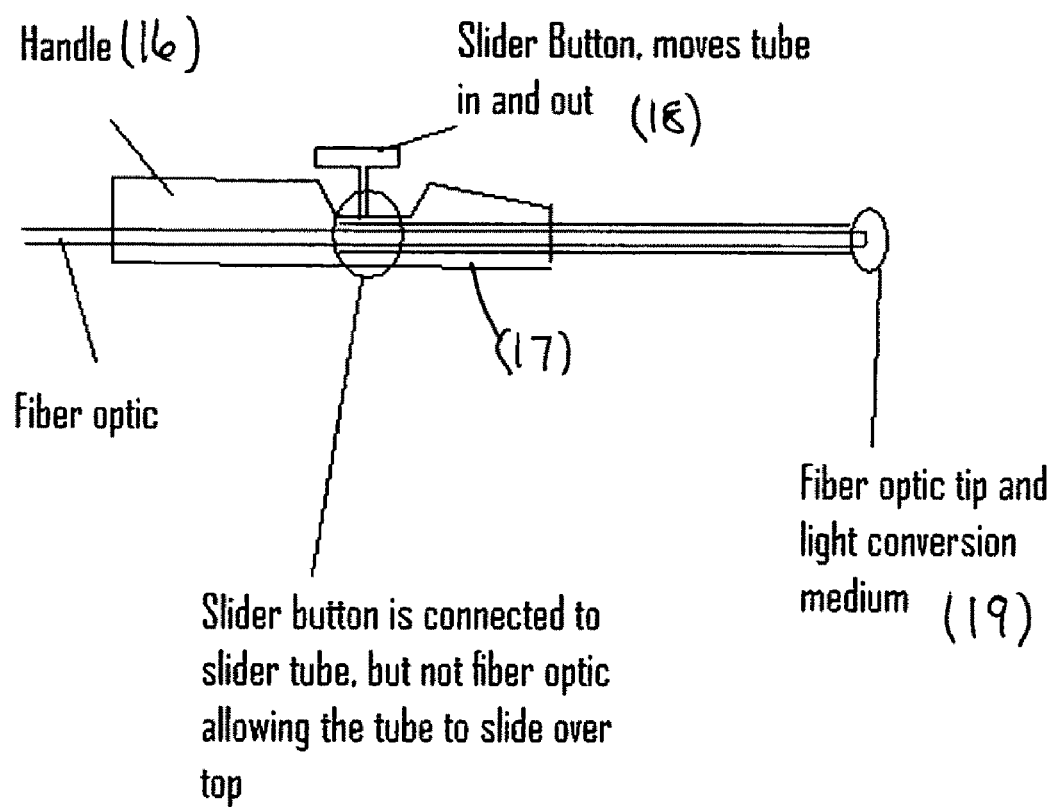
FIG. 4 is a schematic diagram of an embodiment of the illumination device with a slider mechanism for controlling the brightness and cone angle of the light.

The illumination device of the present invention may optionally include an adjustable tip that allows the operator to slide a needle over top of the output from the conversion medium or slide the fiber underneath the fixed needle. This permits control of the brightness and cone angle of the light coming out by a simple thumb slider. In addition brightness and cone angle control, slight variation of the color output can be achieved. The color can be varied from a yellowish tone to a bluish tone depending on how much of the conversion medium is exposed. The brightness and cone angle may also be controlled electronically or optically. By varying the input current to the laser power supply the brightness of the laser and thus the output light can be controlled. The brightness may also be controlled optically by using the polarization effects of the laser. By inserting a cross polarizer into the optical path brightness may be controlled. The cone angle can also be controlled optically by using telescoping optical components or adaptive optics. One embodiment of a mechanism for controlling light output of the illumination device is shown in FIG. 4 which shows a handle (16) comprising a slider tube (17) and a slider button (18) which allows the tube to move the tube relative to the fiber optic and light conversion medium (19) such that the brightness and cone angle of the light emitted from the device may be controlled.

Since the light source is laser based other characteristics can be utilized. The laser may be modulated and a detector may be added to the device to get information back from the target object. It is possible to get distance, size, position, temperature or other information. This could be added to a robotic surgical device to obtain more accurate information. This information could be useful to a physician to more accurately complete a procedure.

The devices of the present invention can be used for illumination in various applications including but not limited to endoscopy, laparoscopy, boroscopy, ear, nose, throat surgery, urology, gastroenterology, gynecology, cardiology, cystoscopy. Preferred applications are those that require bright illumination in a confined area such as in vitreoretinal surgery. Particular applications include surgery for diabetic retinopathy, macular degeneration, retinal detachment, macular holes and other vitreo-retinal disorders.

I claim:

1. An illumination device comprising:
   a. a laser light source;
   b. a power supply for supplying power to the laser light source;
   c. a trunk optical fiber operably linked to the laser light source such that the light from the laser light source travels through the trunk optical fiber;
   d. a detachable fiber optic tip operably linked to the trunk optical fiber through a quick connect mechanism such that the light from the trunk optical fiber travels through the fiber optic tip; and
   e. a light conversion medium disposed at the distal end of the fiber optic tip operably linked to the fiber optic tip such that the laser light excites the light conversion medium to produce illumination light.

2. The illumination device of claim 1 wherein the output angle is from about 80 to about 360 degrees full angle.

3. The illumination device of claim 1 further comprising a protective jacket which encompasses the trunk optical fiber.

4. The illumination device of claim 1 further comprising a quick connect mechanism to operably link the trunk optical fiber to the detachable fiber optic tip.

5. The illumination device of claim 4 wherein the laser light source is a Neodymium YAG laser.

6. The illumination device as in any of claims 1, or 3 wherein the laser light source produces light with a wavelength between about 473 nm to about 488 nm.

7. The illumination device of claim 6 wherein the phosphor is contained within a polymer medium.

8. The illumination device as in any of claims 1, 3, or 4 wherein the light conversion medium is a phosphor.

9. The illumination device of claim 8 wherein the phosphor is biocompatible.

10. The illumination device of claim 9 wherein the phosphor does not contain lead.

11. The illumination device of claim 10 wherein the phosphor is a Eu-doped silicate phosphor.

12. The illumination device of claim 1 wherein the illumination light can produce a total light outputs of about 1 to about 1600 lumens.

13. The illumination device of claim 12 wherein the illumination light can produce a total light outputs of about 30 to about 100 lumens.

14. The illumination device as in any of claims 1, 3, or 4 further comprising a thumb slider that permits the control of the brightness and cone angle of the illumination light.

15. The illumination device of claim 12 wherein the illumination light can produce a total light outputs of about 10 to about 400 lumens.

16. The illumination device of claim 1 further comprising a glass capillary used to house the light conversion medium and the fiber optic tip.

17. The illumination device of claim 1 wherein the output angle is greater than 0.66 numerical aperture.

18. The illumination device of claim 17 wherein the illumination light has an output of at least 400 lumens in about a 350 um diameter cross-sectional area.

19. An illumination device of use in vitreo-retinal surgery comprising:
   a. a laser light source that emits a wavelength of between about 473 and 488 nm;
   b. a power supply for supplying power to the laser light source;
   c. a trunk optical fiber operably linked to the laser light source such that the light from the laser light source travels through the trunk optical fiber;
   d. a detachable fiber optic tip operably linked to the trunk optical fiber through a quick connect mechanism such that the light from the trunk optical fiber travels through the detachable fiber optic tip; and
   e. a Eu-doped silicate phosphor disposed at the distal end of the detachable fiber optic tip operably linked to the disposable fiber optic tip such that the laser light excites the light conversion medium to produce illumination light;
   f. a 23 gauge needle which houses the detachable fiber optic tip; and
   g. a slider mechanism wherein the slider mechanism permits the control of the brightness and cone angle of the illumination light.

* * * * *